(12) United States Patent
Wake

(10) Patent No.: US 10,827,908 B2
(45) Date of Patent: Nov. 10, 2020

(54) ENDOSCOPE APPARATUS AND ENDOSCOPE HAVING VALVE WHICH IS OPENED AND CLOSED BASED ON OPERATION OF CAUTERIZING DEVICE

(71) Applicant: OLYMPUS CORPORATION, Tokyo (JP)

(72) Inventor: Fuminori Wake, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 494 days.

(21) Appl. No.: 15/792,837

(22) Filed: Oct. 25, 2017

(65) Prior Publication Data

US 2018/0055340 A1 Mar. 1, 2018

Related U.S. Application Data

(63) Continuation of application No. PCT/JP2016/061235, filed on Apr. 6, 2016.

(30) Foreign Application Priority Data

Apr. 30, 2015 (JP) .................................. 2015-093367

(51) Int. Cl.
| | | |
|---|---|---|
| *A61B 1/00* | (2006.01) | |
| *A61B 1/015* | (2006.01) | |
| *A61B 17/32* | (2006.01) | |
| *A61B 1/018* | (2006.01) | |
| *A61B 5/021* | (2006.01) | |

(Continued)

(52) U.S. Cl.
CPC ............ *A61B 1/00094* (2013.01); *A61B 1/00* (2013.01); *A61B 1/00068* (2013.01); *A61B 1/015* (2013.01); *A61B 1/0125* (2013.01); *G02B 23/24* (2013.01); *A61B 1/0052* (2013.01); *A61B 1/00091* (2013.01); *A61B 1/00101* (2013.01); *A61B 1/01* (2013.01); *A61B 1/018* (2013.01); *A61B 1/042* (2013.01); *A61B 1/045* (2013.01);

(Continued)

(58) Field of Classification Search
None
See application file for complete search history.

(56) References Cited

U.S. PATENT DOCUMENTS

| | | | | |
|---|---|---|---|---|
| 5,879,288 A | * | 3/1999 | Suzuki | ............... A61B 1/00068 |
| | | | | 600/121 |
| 2002/0040181 A1 | * | 4/2002 | Arai | ...................... A61B 1/127 |
| | | | | 600/156 |

(Continued)

FOREIGN PATENT DOCUMENTS

| | | |
|---|---|---|
| EP | 1726255 A2 | 11/2006 |
| JP | H05-285094 A | 11/1993 |

(Continued)

OTHER PUBLICATIONS

International Search Report dated Jun. 14, 2016 issued in PCT/JP2016/061235.

*Primary Examiner* — John P Leubecker
*Assistant Examiner* — Minqiao Huang
(74) *Attorney, Agent, or Firm* — Scully, Scott, Murphy & Presser, P.C.

(57) ABSTRACT

An endoscope apparatus includes: an endoscope including an insertion portion, a suction conduit, a by-pass conduit, a suction button, and a solenoid valve; a high-frequency knife; and a valve opening/closing portion.

12 Claims, 8 Drawing Sheets

(51) Int. Cl.
*A61B 1/045* (2006.01)
*G02B 23/24* (2006.01)
*A61B 1/012* (2006.01)
*A61B 1/04* (2006.01)
*A61B 1/005* (2006.01)
*A61B 1/01* (2006.01)

(52) U.S. Cl.
CPC ............ *A61B 5/02141* (2013.01); *A61B 2017/320095* (2017.08)

(56) References Cited

U.S. PATENT DOCUMENTS

| | | | | |
|---|---|---|---|---|
| 2006/0047185 | A1* | 3/2006 | Shener | A61B 1/00068 600/156 |
| 2006/0266423 | A1* | 11/2006 | Akiba | A61M 3/0258 137/565.01 |
| 2007/0005002 | A1* | 1/2007 | Millman | A61M 1/0058 604/30 |
| 2009/0209822 | A1* | 8/2009 | Ikeda | A61B 1/00101 600/157 |
| 2012/0088974 | A1* | 4/2012 | Maurice | A61B 1/127 600/157 |
| 2012/0101339 | A1* | 4/2012 | Brannon | A61B 1/015 600/158 |
| 2015/0133779 | A1* | 5/2015 | Yurek | A61B 8/12 600/435 |
| 2015/0216393 | A1* | 8/2015 | Toyoda | A61B 1/015 600/159 |
| 2015/0290403 | A1* | 10/2015 | Torisawa | A61B 17/3474 604/26 |
| 2016/0089002 | A1* | 3/2016 | Burton | A61B 1/00068 600/154 |
| 2017/0079520 | A1* | 3/2017 | Huang | A61B 1/00135 |

FOREIGN PATENT DOCUMENTS

| | | |
|---|---|---|
| JP | H06209950 A | 8/1994 |
| JP | H09140722 A | 6/1997 |
| JP | 2006325813 A | 12/2006 |
| JP | 2007105395 A | 4/2007 |

* cited by examiner

ENDOSCOPE APPARATUS AND ENDOSCOPE HAVING VALVE WHICH IS OPENED AND CLOSED BASED ON OPERATION OF CAUTERIZING DEVICE

CROSS REFERENCE TO RELATED APPLICATION

This application is a continuation application of PCT/JP2016/061235 filed on Apr. 6, 2016 and claims benefit of Japanese Application No. 2015-093367 filed in Japan on Apr. 30, 2015, the entire contents of which are incorporated herein by this reference.

BACKGROUND OF THE INVENTION

1. Field of the Invention

The present invention relates to an endoscope apparatus that includes an endoscope including inside thereof a first conduit and a cauterizing device that applies energy to a living tissue in a body cavity to cauterize the living tissue, and an endoscope.

2. Description of the Related Art

In endoscope apparatuses for use in medical fields, a method and a configuration are well-known in which fluids in a body cavity, for example, liquids in the body cavity such as mucus and cleaning water used for cleaning an optical system, and solid substances in the body cavity such as residue and a tissue to be treated that is resected with a treatment instrument are removed by using a suction conduit, as a first conduit serving also as a treatment instrument insertion channel, which is provided in an endoscope and to which a suction device is connected. An object of such a method and a configuration is to ensure a good observation field of view of an endoscope when observation of a living tissue in a body cavity is performed by inserting an insertion portion of the endoscope into the body cavity.

Japanese Patent Application Laid-Open Publication No. 2007-105395 discloses a configuration in which a suction port of a suction conduit is open on a distal end surface of a distal end in a longitudinal direction of an insertion portion of an endoscope (hereinafter, just referred to as distal end), a part of the suction conduit is branched off and open on an operation portion of the endoscope, as a treatment instrument insertion port, furthermore, a connecting connector for connecting the endoscope with an external apparatus (hereinafter, just referred to as connector) includes a pipe sleeve to which a suction device is connected, the pipe sleeve communicating with an opening located on the proximal end in the longitudinal direction of the suction conduit (hereinafter, just referred to as proximal end), and after the suction device is driven, fluids in the body cavity are sucked from the suction port through the suction conduit.

In endoscope apparatuses for use in medical fields, a procedure is well-known in which, in a state where an insertion portion of an endoscope is inserted into a body cavity and a tissue to be treated of a living tissue in the body cavity is observed under the observation with the endoscope, a cauterizing device, which is inserted into a suction conduit through a treatment instrument insertion port provided at an operation portion of the endoscope, is protruded from a suction port provided at the insertion portion, and the tissue to be treated is dissected and resected from the living tissue by applying energy from the protruded cauterizing device to the tissue to be treated.

As one example, an ESD (endoscopic submucosal dissection) procedure, for example, is well-known in a surgical treatment for removing a lesional part such as a carcinoma tissue in a body cavity under the observation with an endoscope.

Specifically, the ESD procedure is known as a treatment in which, for example, in a state where an insertion portion of an endoscope is inserted into a body cavity and a carcinoma tissue that exists in the body cavity is within an observation field of view of the endoscope, a cauterizing device, for example, a high-frequency knife inserted into a suction conduit of the endoscope is protruded forward in the longitudinal direction (hereinafter, just referred to as forward) from the distal end of the insertion portion, and then, the insertion portion is moved forward and backward in the longitudinal direction to thereby remove the carcinoma tissue that has been floated in advance by injecting a specialized-purpose liquid, through the use of the high-frequency knife.

During the procedure for incising a living tissue and coagulating bleeding, such as the ESD procedure, for example, mucus and fat in a body cavity are likely to evaporate with the incision and the coagulation performed by high-frequency current being applied from a high-frequency knife to the carcinoma tissue, and the mucosa and the fat are turned into mist as a fluid including solid particulate components, more specifically, a gas including components derived from the living tissue.

As a result, in a procedure that lasts for hours, such as the ESD procedure, in particular, circumstances in which the narrow body cavity is likely to be filled with mist and the observation field of view of the endoscope is blocked may occur. In order to ensure the observation field of view during the ESD procedure, it is preferable to use a method of sucking the gas including the components derived from the living tissue from the suction port, through the use of the suction conduit in the endoscope apparatus disclosed in the Japanese Patent Application Laid-Open Publication No. 2007-105395.

SUMMARY OF THE INVENTION

An endoscope apparatus according to one aspect of the present invention includes: an endoscope which includes: an insertion portion having a distal end and a proximal end, and inserted into a body from a distal end side; a first conduit for allowing fluids in the body to flow to outside the body through a suction port provided at the distal end side of the insertion portion; a second conduit through which, among the fluids in the body, a fluid generated in the body and including a solid particulate component passes, the second conduit being provided so as to be branched off from a halfway position of the first conduit and joined again with the first conduit; a first valve that opens and closes a flow passage of the first conduit, the first valve being provided to the first conduit at a location between a position where the second conduit is branched off and a position where the second conduit is joined; and a second valve that opens and closes a flow passage of the second conduit, the second valve being provided to the second conduit; a cauterizing device that applies energy to a living tissue in the body to cauterize the living tissue; and a valve opening/closing portion that causes the second valve to open and close based on an operation of the cauterizing device.

Further, an endoscope apparatus according to another aspect of the present invention includes: an endoscope which includes: an insertion portion having a distal end and a proximal end, and inserted into a body from a distal end side; a first conduit for allowing fluids in the body to flow to outside the body through a suction port provided at the distal end side of the insertion portion; a second conduit through which, among the fluids in the body, a fluid generated in the body and including a solid particulate component passes, the second conduit being provided so as to be branched off from a halfway position of the first conduit and joined again with the first conduit; a first valve that opens and closes a flow passage of the first conduit, the first valve being provided to the first conduit at a location between a position where the second conduit is branched off and a position where the second conduit is joined; and a second valve that opens and closes a flow passage of the second conduit, the second valve being provided to the second conduit; and a cauterizing device that applies energy to a living tissue in the body to cauterize the living tissue, and the endoscope apparatus further includes a valve opening/closing portion of the endoscope that performs control for opening/closing the second valve based on an operation of the cauterizing device.

Furthermore, an endoscope according to one aspect of the present invention includes: an insertion portion having a distal end and a proximal end, and inserted into a body from a distal end side; a first conduit for allowing fluids in the body to flow to outside the body through a suction port provided at the distal end side of the insertion portion; a second conduit through which, among the fluids in the body, a fluid generated in the body and including a solid particulate component passes, the second conduit being provided so as to be branched off from a halfway position of the first conduit and joined again with the first conduit; a first valve that opens and closes a flow passage of the first conduit, the first valve being provided to the first conduit at a location between a position where the second conduit is branched off and a position where the second conduit is joined; and a second valve that opens and closes a flow passage of the second conduit, the second valve being provided to the second conduit; wherein the second valve is opened and closed based on an operation of a cauterizing device that cauterizes a living tissue in the body by applying energy to the living tissue.

DETAILED DESCRIPTION OF THE PREFERRED EMBODIMENTS

Hereinafter, embodiments of the present invention will be described with reference to drawings. Note that the drawings are schematic, and care should be taken to the fact that the relationship between the thicknesses and widths of the respective members, a ratio of the thickness of a certain member to that of another member, and the like are different from the actual ones. It is needless to say that each of the drawings includes a part in which the relationship and ratio among the dimensions are different from those in other drawings.

First Embodiment

Figure 1:
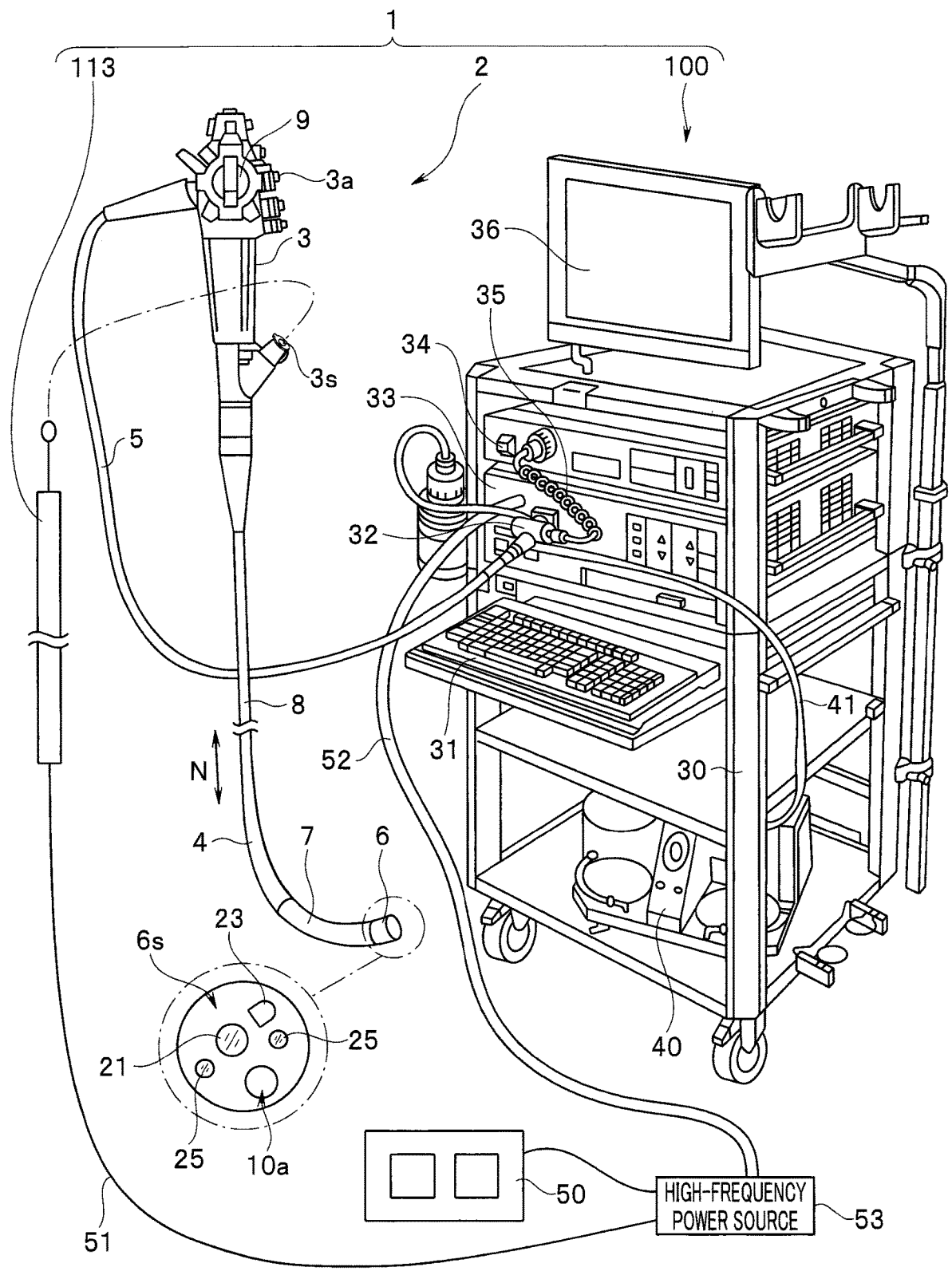
FIG. 1 schematically illustrates an endoscope apparatus according to a present embodiment.
Figure 2:
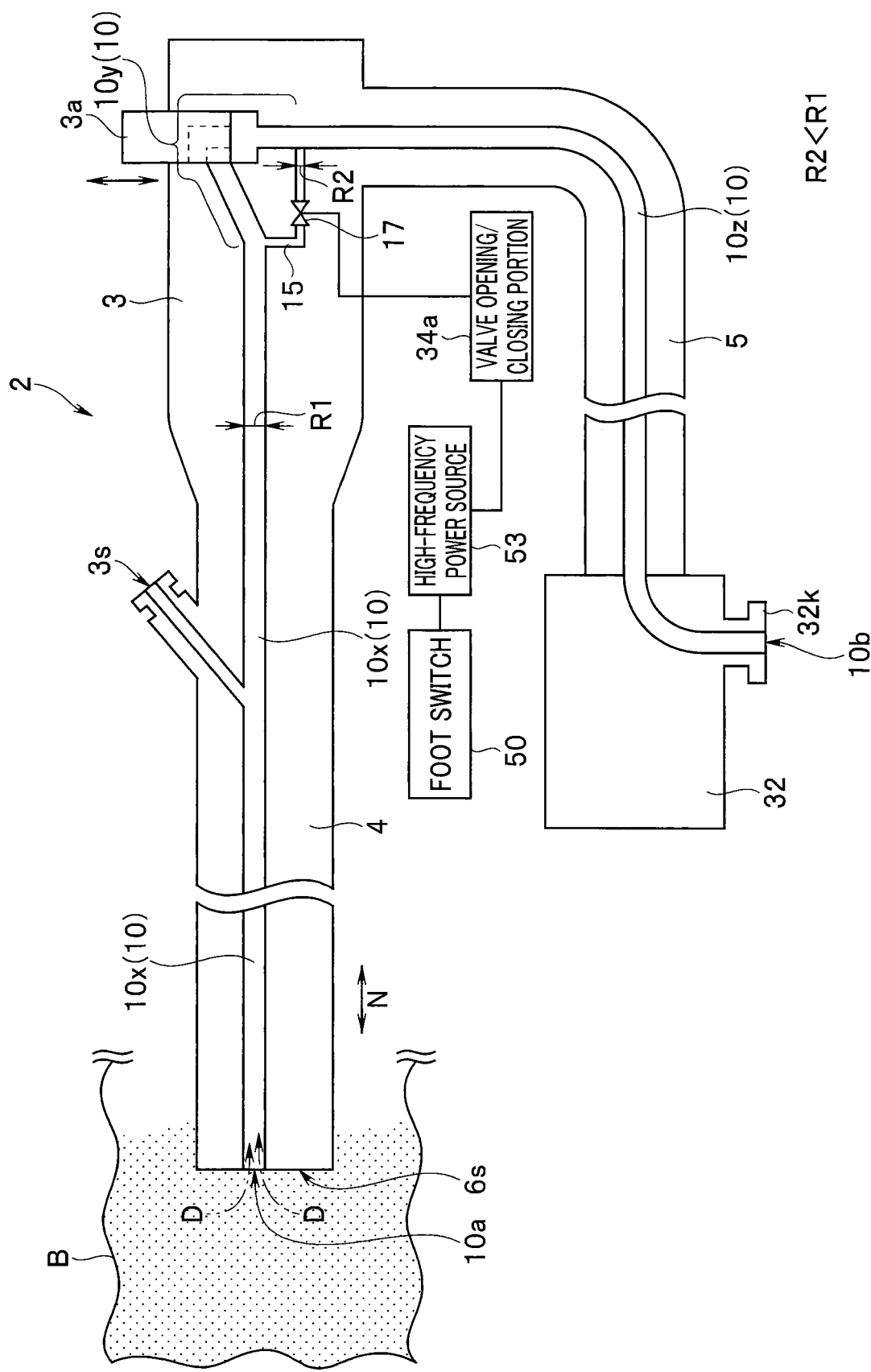
FIG. 2 schematically illustrates a first conduit and a second conduit provided in an endoscope in the endoscope apparatus in FIG. 1 together with a conduit opening/closing portion and a foot switch, with an insertion portion being inserted into a body cavity.

FIG. 1 schematically illustrates an endoscope apparatus according to a present embodiment. FIG. 2 schematically illustrates a first conduit and a second conduit provided in an endoscope in the endoscope apparatus in FIG. 1 together with a conduit opening/closing portion and a foot switch, with an insertion portion being inserted into a body cavity.

As shown in FIG. 1, an endoscope apparatus 1 includes an endoscope 2, a peripheral apparatus 100 and a cauterizing device 113.

The peripheral apparatus 100 includes a keyboard 31, a light source device 33, a video processor 34, a monitor 36, and a suction device 40 that are placed on a rack 30.

The main part of the endoscope 2 is configured by including an insertion portion 4 to be inserted into a body cavity B (see FIG. 2), an operation portion 3 provided continuously with the proximal end of the insertion portion 4, a universal cord 5 extended from the operation portion 3, and a connector 32 provided at the extension end of the universal cord 5 and attachable to and detachable from the light source device 33.

Note that the connector 32 and the video processor 34 are electrically connected to each other with a connection cable 35.

The insertion portion 4 is configured by a distal end portion 6 located on a distal end side in a longitudinal direction N of the insertion portion 4 (hereinafter, just referred to as distal end side), a bending portion 7 provided continuously with the proximal end of the distal end portion 6 and operated to be bent in four directions, i.e., up, down, left and right directions by a bending operation knob 9 provided at the operation portion 3, and a flexible tube portion 8 provided continuously with the proximal end of the bending portion 7.

On the distal end surface 6s of the distal end portion 6, a suction port 10a of a suction conduit 10 (see FIG. 2) as a first conduit, an objective lens 21 as an optical system that configures an object image acquiring section, not shown, provided in the distal end portion 6, an air/water feeding nozzle 23, an illumination window 25, and the like are arranged.

Note that the object image acquiring section, as is well known, picks up an image in the body cavity B, and includes a main part configured by an optical system, not shown, including the objective lens 21 exposed on the distal end surface 6s or a plurality of lenses including the objective lens 21, and an image pickup device, not shown, in which the image of an object focused by the optical system is formed.

The air/water feeding nozzle 23 supplies a fluid to the objective lens 21, to remove the filth adhered to the objective lens 21 or supplies a fluid into the subject.

The illumination window 25 is a part through which illumination light is supplied into the body cavity B. Note that a light-emitting element such as LED may be provided on the distal end surface 6s, instead of the illumination window 25.

As shown in FIG. 2, the suction port 10a configures the opening at the distal end of the suction conduit 10 provided through the insertion portion 4, the operation portion 3, the universal cord 5, and the connector 32. The suction conduit 10 is branched off in the operation portion 3, and one branched part is open as a treatment instrument insertion port 3s on the operation portion 3.

Furthermore, an opening 10b at the proximal end of the connector 32 of the suction conduit 10 is provided at a suction pipe sleeve 32k, and the suction pipe sleeve 32k is connected with a suction tube 41 (see FIG. 1) extended from a suction device 40.

When a suction button 3a which is a first valve provided on the operation portion 3 is depressed, the suction conduit 10, together with the suction tube 41 communicated with the suction conduit 10 via the suction port 10a, sucks the fluids in the body cavity B, for example, liquids in the body cavity B such as the mucus and the cleaning water used for cleaning the objective lens 21, and the solid substances in the body cavity B such as the residue and the tissue to be treated that is resected with various kinds of treatment instruments such as the cauterizing device 113, by the driving of the suction device 40. In addition, various kinds of treatment instruments are introduced into the suction conduit 10 through the treatment instrument insertion port 3s, and the suction conduit 10 allows the introduced various kinds of treatment instruments to pass therethrough and protrude into the body cavity B through the suction port 10a. That is, the suction conduit 10 also serves as a treatment instrument insertion channel.

Note that the cauterizing device 113 applies energy to the living tissue in the body cavity B to cauterize the living tissue, and configured by a high-frequency knife, for example. Hereinafter, the high-frequency knife is also denoted by the reference numeral 113.

In addition, as shown in FIG. 2, the high-frequency knife 113 is electrically connected with a valve opening/closing portion 34a, which is provided, for example, in the video processor 34 and which controls opening and closing states of a solenoid valve 17 to be described later, and the high-frequency knife 113 is supplied with power from a high-frequency power source 53.

In addition, as shown in FIGS. 1, 2, the high-frequency power source 53 is connected with a foot switch 50 that is operated by stepping-on operation by an operator.

As shown in FIG. 2, the suction button 3a is provided at the halfway position of the suction conduit 10 at a location 10y, which is between a position where a by-pass conduit 15 to be described later is branched off from the suction conduit 10 and a position where the by-pass conduit 15 is joined with the suction conduit 10, and the suction button 3a is for opening and closing a flow passage of the suction conduit 10.

Specifically, the suction button 3a is a valve for opening and closing the flow passage of the suction conduit 10 actively by the operation of the operator, and the suction button 3a is depressed by the operator to open the flow passage of the suction conduit 10.

That is, the flow passage of the suction conduit 10 which is located on the distal end side with respect to the suction button 3a and the flow passage of suction conduit 10 which is located on the proximal end side in the longitudinal direction N (hereinafter, just referred to as proximal end side) are not communicated with each other when the suction button 3a is not operated. The distal end side flow passage and proximal end side flow passage of the suction conduit 10 are configured to be communicated with each other only when the depression operation of the suction button 3a is performed by the operator.

Note that, since the suction device 40 is constantly driven, the fluid in the body cavity B is sucked through the suction conduit 10, which is communicating from the suction port 10a to the opening 10b located at the proximal end, and the suction tube 41, only when the depression operation of the suction button 3a is performed.

In addition, as shown in FIG. 2, in the operation portion 3 of the endoscope 2, the by-pass conduit 15, which is a second conduit, is provided so as to be branched off from the halfway position of the suction conduit 10 and joined again with the suction conduit 10.

The by-pass conduit 15 is a conduit through which, among the fluids in the body cavity B, the fluid including the solid particulate components, which is filled in the body cavity B, is passed by the driving of the suction device 40.

Specifically, the by-pass conduit 15 is a conduit through which the mist gas D including the components derived from the living tissue cauterized by the energy being applied thereto from the high-frequency knife 113 is passed via the suction port 10a and a part 10x of the suction conduit 10, which is located on the distal end side with respect to the by-pass conduit 15, by the driving of the suction device 40.

Note that the gas D including the components derived from the living tissue, which is filled in the body cavity B, is the gas including the components such as the mucosa, fat, and the like that constitute the living tissue in the body cavity B which is cauterized by the energy being applied thereto by the high-frequency knife 113 protruded into the body cavity B via the treatment instrument insertion port 3s, the suction conduit 10, and the suction port 10a, during the above-described ESD procedure, for example, as shown in FIG. 2.

Hereinafter, one example of the above-described ESD procedure will be briefly described with reference to FIGS. 3A to 3D, FIG. 4A, and FIG. 4B.

Figure 3A:
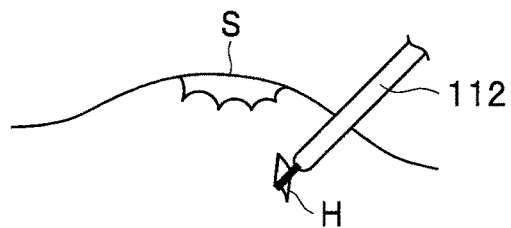
FIG. 3A is a perspective view showing a procedure for boring a hole on a mucosa around a lesional mucosa part by using an incision tool.
Figure 3B:
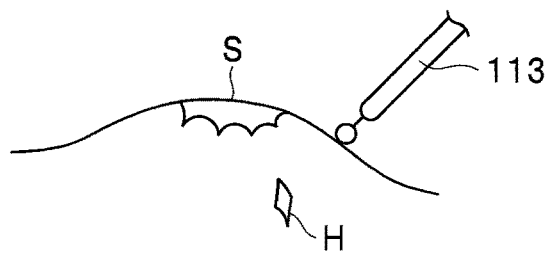
FIG. 3B is a perspective view showing a state where a high-frequency knife is protruded in a body cavity through another suction conduit of the endoscope.
Figure 3C:
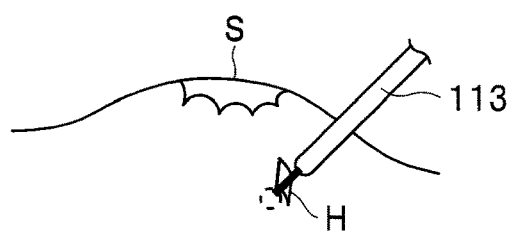
FIG. 3C is a perspective view showing a state where a distal end of the high-frequency knife in FIG. 3B is inserted into the hole bored by the incision tool.
Figure 3D:
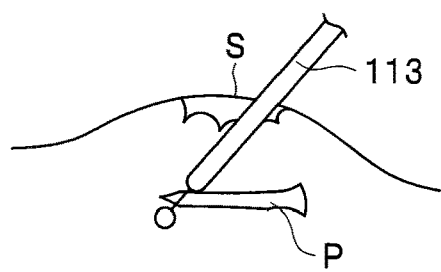
FIG. 3D is a perspective view showing an incision operation of the lesional mucosa part with the high-frequency knife.

FIGS. 3A to 3D are perspective views schematically describing one example of the incision operation of the lesional mucosa part in the ESD procedure performed by inserting the insertion portion of the endoscope shown in FIG. 1 into the body cavity and using the incision tool and the high-frequency knife protruded from another suction conduit of the endoscope. FIG. 3A is a perspective view showing a procedure for boring a hole on the mucosa around the lesional mucosa part by using the incision tool. FIG. 3B is a perspective view showing the state where the high-frequency knife is protruded in the body cavity through the other suction conduit of the endoscope. FIG. 3C is a perspective view showing the state where the distal end of the high-frequency knife in FIG. 3B is inserted into the hole bored by the incision tool. FIG. 3D is a perspective view showing the incision operation of the lesional mucosa part by the high-frequency knife.

Figure 4A:
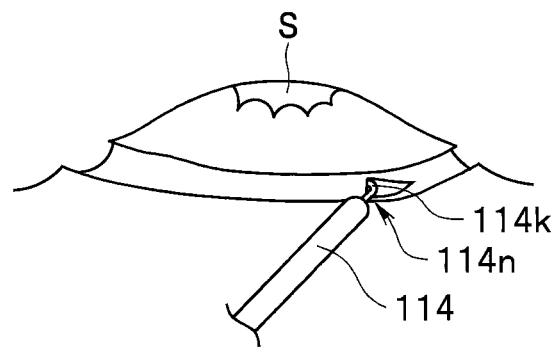
FIG. 4A is a perspective view showing a state where a distal end of a dissection tool is hooked on a slit formed by the incision with the high-frequency knife.
Figure 4B:
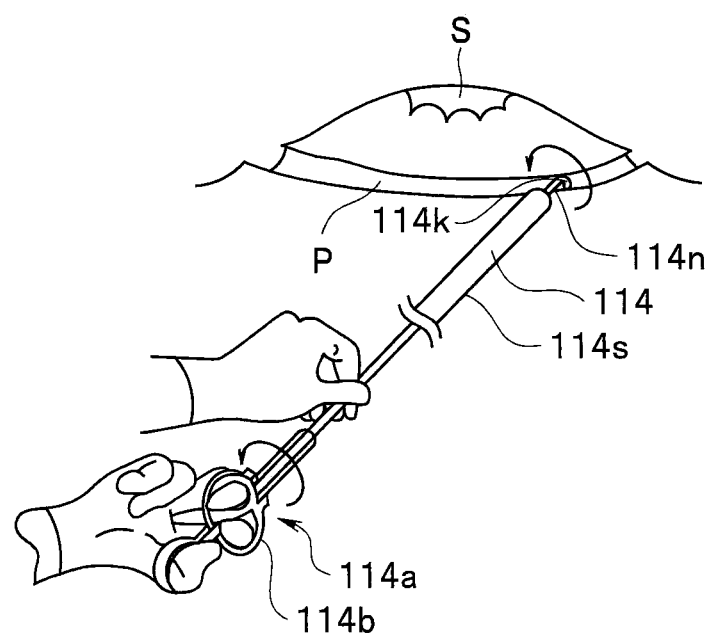
FIG. 4B is a perspective view showing an adjusting operation of a direction of a flexing portion of the dissection tool in FIG. 4A.

In addition, FIGS. 4A and 4B are perspective views schematically describing the dissection operation of the lesional mucosa part in the ESD procedure using the dissection tool protruded from another suction conduit of the endoscope shown in FIG. 1. FIG. 4A is a perspective view showing the state where the distal end of the dissection tool is hooked on the slit formed by the incision with the high-frequency knife. FIG. 4B is a perspective view showing the adjusting operation of the direction of the flexing portion of the dissection tool in FIG. 4A.

First, the operator introduces the insertion portion 4 of the endoscope 2 into the body cavity, and injects normal saline into the submucosal layer of the lesional mucosa part S which is a tissue to be treated by using an injection needle, not shown, protruded from the suction port 10a into the body cavity via the treatment instrument insertion port 3s and the suction conduit 10, to cause the lesional mucosa part S to be raised as shown in FIG. 3A.

Next, as shown in FIG. 3A, the operator bores a hole H on a part of the mucosa around the lesional mucosa part S using the incision tool 112 protruded from the suction port 10a into the subject.

After that, the operator extracts the incision tool 112 from the suction conduit 10, and inserts the knife distal end of the high-frequency knife 113, which is protruded from the suction port 10a into the body cavity via the treatment instrument insertion port 3s and the suction conduit 10, as shown in FIG. 3B, into the hole H as shown in FIG. 3C.

In this state, as shown in FIG. 3D, the operator moves the distal end side of the insertion portion 4 forward and backward about 20 mm to 50 mm, for example, also with the aid of the bending of the bending portion 7, while supplying the high-frequency current to the knife distal end, to thereby move also the distal end side of the high-frequency knife 113 about 20 mm to 50 mm, incise the perimeter of the lesional mucosa part S, and form the slit P.

Next, the operator incises the lesional mucosa part S over the entire circumference thereof, and thereafter extracts the high-frequency knife 113 from the suction conduit 10. Then, as shown in FIG. 4A, the operator introduces, into the body cavity, the dissection tool 114 which is protruded from the suction port 10a into the body cavity via the treatment instrument insertion port 3s and the suction conduit 10, and causes a knife portion 114n to abut the slit P. Then, the operator hooks the flexing portion 114k on the slit P to incise and dissect the lower layer of the lesional mucosa part S. At this time, it is preferable that the flexing portion 114k is parallel to the muscularis propria or directed toward the inner cavity side.

Note that, when the flexing portion 114k is directed in an undesired direction, the operator adjusts the direction of the flexing portion 114k. Specifically, as shown in FIG. 4B, the operator grasps the sheath 114s to rotate the operation portion 114a, with an operation slider 114b of the operation portion 114a being moved slightly backward. Then, the operator changes the direction of the flexing portion 114k, and thereafter moves the operation slider 114b forward, to thereby restrict the rotational movement of the knife portion 114n by a known mechanism. As a result, the flexing portion 114k is fixed, with the direction thereof being maintained, during the resection and dissection of the mucosa.

Finally, the operator resects and dissects all of the lesional mucosa part S, and thereafter extracts the dissection tool 114 from the suction conduit 10 and takes out the lesional mucosa part S through the suction conduit 10 by using a grasping forceps, or the like, not shown, which is protruded from the suction port 10a into the body cavity via the treatment instrument insertion port 3s and the suction conduit 10.

In the ESD procedure shown in FIGS. 3A to 3D, FIG. 4A, and FIG. 4B, the mist gas D including the components derived from the living tissue, which is generated and filled in the body cavity B when the perimeter of the lesional mucosa part S is resected by using the high-frequency knife 113, passes through the by-pass conduit 15, as shown in FIG. 3D. Note that the gas D passed through the by-pass conduit 15 flows into the part 10z located on the proximal end side with respect to the position where the by-pass conduit 15 is joined again with the suction conduit 10.

As shown in FIG. 2, the solenoid valve 17, as the second valve, which opens and closes the flow passage of the by-pass conduit 15 is provided at the halfway position of the by-pass conduit 15.

The high-frequency power source 53 is electrically connected to the valve opening/closing portion 34a, and controls the valve opening/closing portion 34a to perform opening/closing operation on the solenoid valve 17 at the timing based on the operation of the high-frequency knife 113.

Specifically, the valve opening/closing portion 34a performs operation for opening the solenoid valve 17 in conjunction with the timing at which the high-frequency knife 113 applies energy to the living tissue.

That is, the solenoid valve 17 is regularly closed. Only when the operator steps on the foot switch 50 to cause the high-frequency power source 53 to supply power to the high-frequency knife 113, the solenoid valve 17 is supplied with power from the valve opening/closing portion 34a to open.

The solenoid valve 17 is closed when the operator depresses the suction button 3a to suck the fluid in the body cavity B through the suction conduit 10, which prevents the fluid from passing through the by-pass conduit 15.

Note that suction of the gas D through the by-pass conduit 15 as well as the parts 10x, 10z of the suction conduit 10 is performed thoroughly so as to secure excellent observation field of view of the objective lens 21 in the body cavity B. That is, sucking of the gas D prevents the components derived from the living tissue in the gas D from adhering to the objective lens 21 and enables the gas D to be removed from the inside of the body cavity B.

Note that the diameter R2 of the by-pass conduit 15 is formed to be smaller than the diameter R1 of the suction conduit 10, for example, to be equal to or smaller than 1 mm (R1>R2), as shown in FIG. 2. Such a configuration is for the purpose of size reduction of the operation portion 3, and as described above, the by-pass conduit 15 is a conduit provided just for allowing the gas D to pass through. That is, the diameter of the by-pass conduit 15 does not have to be as large as the diameter of the suction conduit 10 through which the solid substances and the like sucked from the body cavity B pass.

In addition, in view of the fact that both of the hands of the operator are occupied while the operator performs the above-described ESD procedure by using the high-frequency knife 113, it is not supposed that the stepping-on operation of the foot switch 50 and the depression operation of the suction button 3a are simultaneously performed by the operator.

In other words, it is not supposed that the gas D and other fluids in the body cavity B are sucked both through the by-pass conduit 15 and the location 10y of the suction conduit 10, which is between the position where the by-pass conduit 15 is branched off from the suction conduit 10 and the position where the by-pass conduit 15 is joined with the suction conduit 10.

Thus, in the present embodiment, the by-pass conduit 15 through which the gas D passes is provided in the operation portion 3 such that the by-pass conduit 15 is branched off from the halfway position of the suction conduit 10 and is joined again with the suction conduit 10.

In addition, the solenoid valve 17 is provided at the halfway position of the by-pass conduit 15, and the solenoid valve 17 opens under the control by the valve opening/closing portion 34a only when the stepping-on operation of the foot switch 50 is performed by the operator to cause the high-frequency power source 53 to supply power to the high-frequency knife 113.

During the ESD procedure, for example, the operator performs the twisting operation of the high-frequency knife 113 and the insertion portion 4 of the endoscope 2 and the rotational moving operation of the bending operation knob 9 substantially simultaneously with both hands, as described above. That is, both hands of the operator are occupied, which makes it difficult for the operator to perform the depression operation of the suction button 3a for performing suction operation of the gas D generated in the body cavity B due to the cauterization of the living tissue with the high-frequency knife 113.

However, according to the configuration of the present embodiment, when power is applied to the high-frequency knife 113, the valve opening/closing portion 34a performs operation for opening the solenoid valve 17 provided at the by-pass conduit 15. That is, when the living tissue is cauterized with the high-frequency knife 113, the valve opening/closing portion 34a opens the solenoid valve 17, which enables the suction operation of the gas D in the body cavity B accompanying the driving of the suction device 40 to be performed through the suction port 10a, the part 10x of the suction conduit 10, which is located on the distal end side with respect to the by-pass conduit 15, the by-pass conduit 15, and the part 10z of the suction conduit 10, which is located on the proximal end side with respect to the by-pass conduit 15.

With such a configuration, when the operator performs the stepping-on operation of the foot switch 50 for applying power to the high-frequency knife 113, the suction operation of the gas D generated in the body cavity B due to the cauterization of the living tissue with the high-frequency knife 113 can be performed automatically and unintentionally, without the depression operation of the suction button 3a by the operator.

Thus, the gas D filled in the narrow body cavity B can be surely removed during the ESD procedure, which enables the excellent observation field of view to be obtained.

In addition, the by-pass conduit 15 through which the gas D is sucked is provided in the operation portion 3 so as to be branched off from the halfway position of the suction conduit 10 and joined again with the suction conduit 10, which eliminates the need for providing an additional conduit for sucking the gas D in the insertion portion 4, to thereby prevent an increase in the diameter size of the insertion portion 4.

The branched part of the suction conduit 10 may be provided in a flexible tube portion 8 in the insertion portion 4 of the endoscope, though not shown. Such a configuration eliminates the need for providing an additional conduit for sucking the gas D in the bending portion 7, which prevents the increase in the diameter size of the bending portion 7 and is capable of maintaining an excellent bending performance of the bending portion 7.

Note that the above-described embodiment is not limited to the ESD procedure but the embodiment can be similarly applied to another method and configuration for dissecting and resecting a tissue to be treated from a living tissue by applying energy from the cauterizing device to the tissue to be treated.

Thus, it is possible to provide the endoscope apparatus 1 capable of smoothly removing the fluid including the solid particulate components, which is filled in the subject, and ensuring the excellent observation field of view of the endoscope 2.

Figure 5:
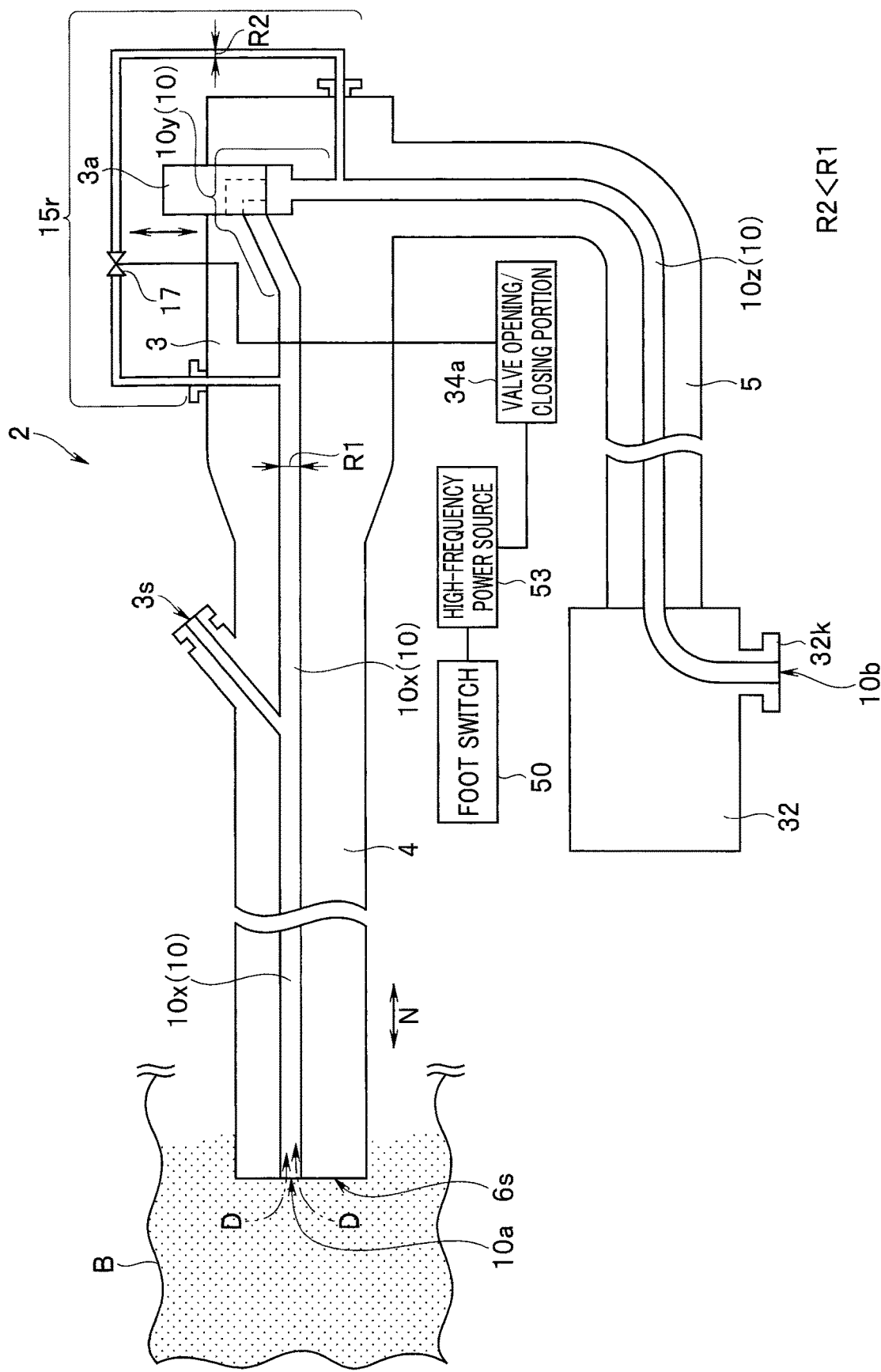
FIG. 5 schematically illustrates a modified example in which a part of a by-pass conduit in FIG. 2 is exposed to an outside of an operation portion, and a solenoid valve is provided at the exposed part.

Note that, hereinafter, a modified example will be described with reference to FIG. 5. FIG. 5 schematically illustrates the modified example in which a part of the by-pass conduit in FIG. 2 is exposed to the outside of the operation portion, and a solenoid valve is provided at the exposed part.

In the above-described embodiment, the by-pass conduit 15 is provided in the operation portion 3.

However, the configuration of the by-pass conduit is not limited to the above-described one, and as shown in FIG. 5, the by-pass conduit 15, which is branched off from the halfway position of the suction conduit 10 and joined again with the suction conduit 10, may have a part exposed to the outside of the operation portion 3, and the solenoid valve 17 may be provided at a part 15r, which is exposed to the outside of the operation portion 3, of the by-pass conduit 15. Also such a configuration is capable of providing the same effects as those in the above-described embodiment, and capable of further reducing the size of the operation portion 3.

Figure 6:
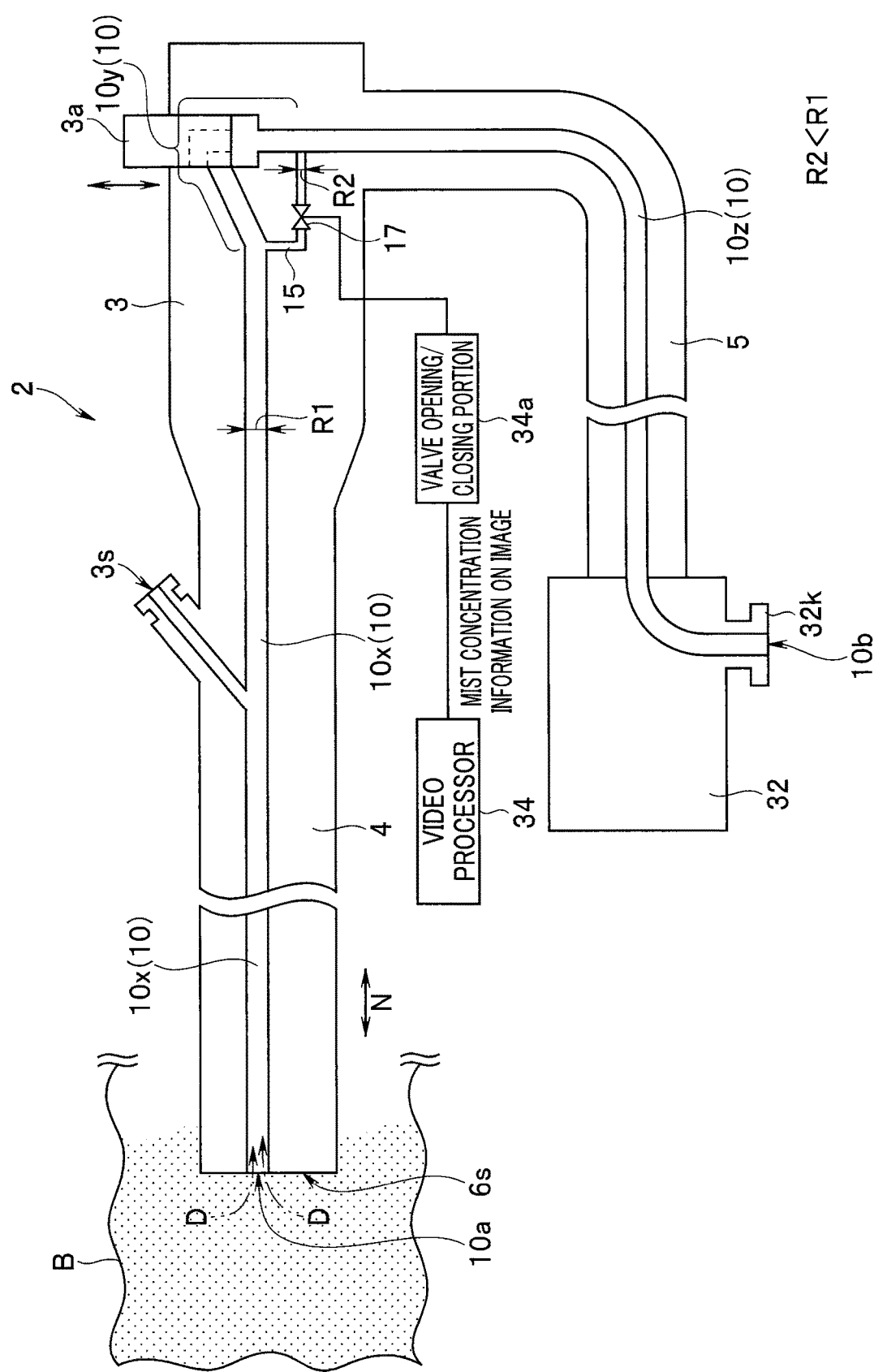
FIG. 6 illustrates a modified example in which a valve opening/closing portion in FIG. 2 opens and closes the solenoid valve based on a determination by a video processor.

FIG. 6 illustrates a modified example in which the valve opening/closing portion in FIG. 2 opens and closes the solenoid valve based on the determination by the video processor.

In addition, not only with the input information that can be obtained from the high-frequency power source but also with the endoscopic image information inputted to the video processor 34 based on the image of the object obtained by the endoscope 2, for example, the video processor 34 may determine, through image processing, that mist of a certain amount or more is generated in the field of view of the endoscope, i.e., a white part is spread over the entire field of view of the endoscope, and may transmit a signal to the valve opening/closing portion 34a to cause the valve opening/closing portion 34a to open and close the solenoid valve 17, as shown in FIG. 6.

Figure 7:
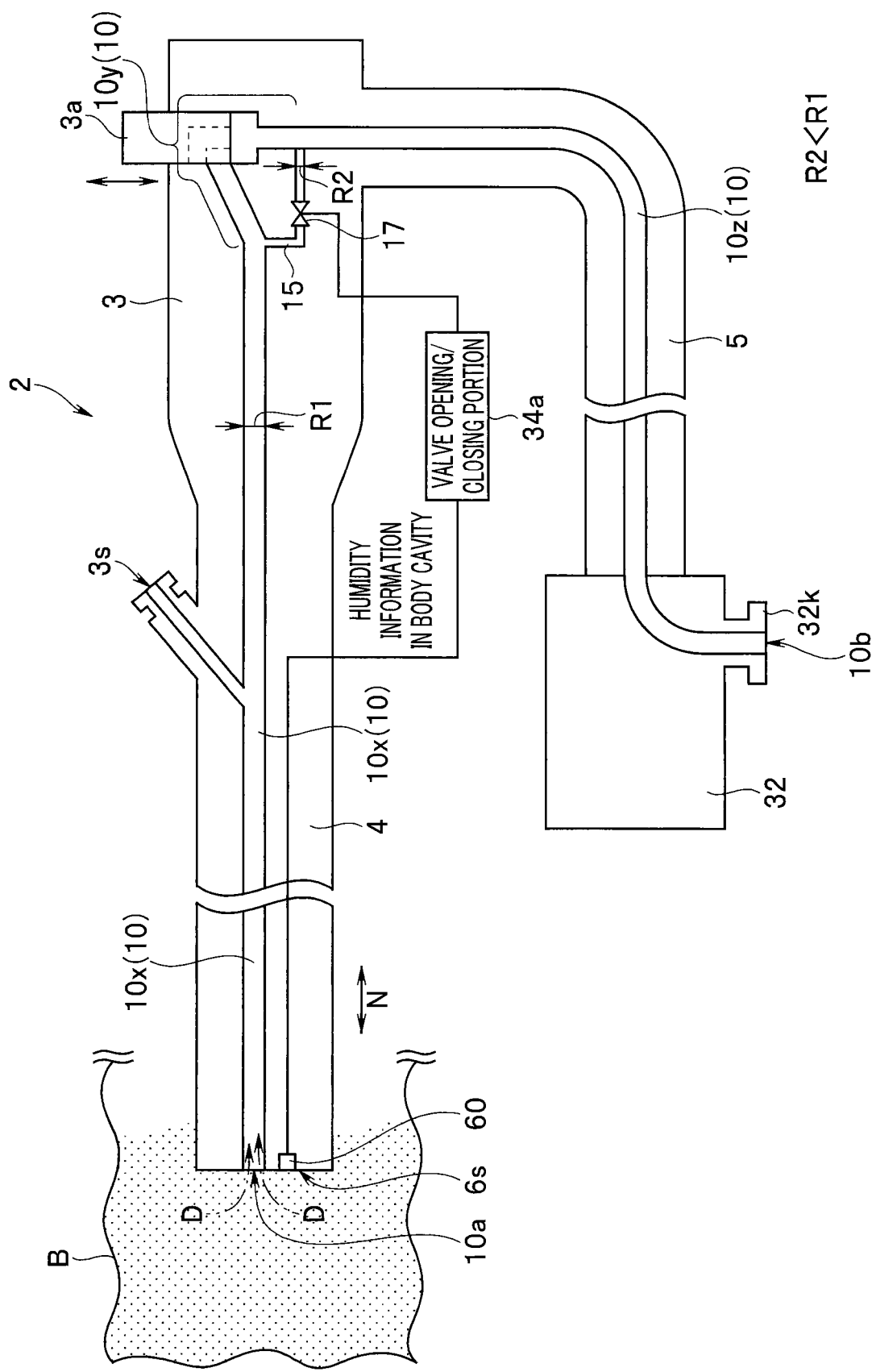
FIG. 7 illustrates a modified example in which the valve opening/closing portion in FIG. 2 opens and closes the solenoid valve based on humidity information obtained from a humidity sensor provided at a distal end portion of the endoscope.

FIG. 7 illustrates a modified example in which the valve opening/closing portion in FIG. 2 opens and closes the solenoid valve based on humidity information obtained by a humidity sensor provided at the distal end portion of the endoscope.

In addition, as shown in FIG. 7, the valve opening/closing portion 34a may open and close the solenoid valve 17 when the humidity in the body cavity becomes equal to or higher than a certain humidity, based on the signal related to the humidity information in the body cavity B which is obtained from a humidity sensor 60 as a humidity detection device provided at the distal end portion 6.

Second Embodiment

Figure 8:
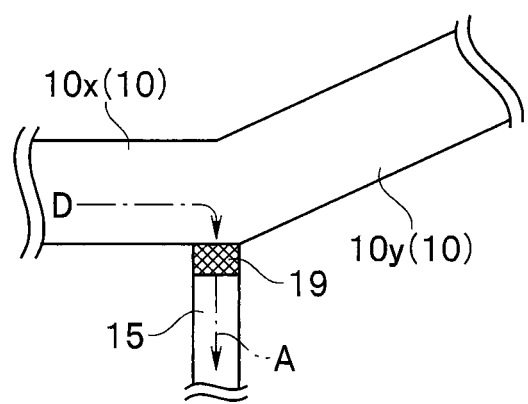
FIG. 8 schematically illustrates, in an enlarged manner, a branched part between a suction conduit and a by-pass conduit that are provided in an endoscope of an endoscope apparatus according to a second embodiment of the present invention.

FIG. 8 schematically illustrates, in an enlarged manner, a branched part between a suction conduit and a by-pass conduit that are provided in an endoscope of an endoscope apparatus according to the present embodiment of the present invention.

The configuration of the endoscope apparatus according to the second embodiment is different from the configuration of the endoscope apparatus according to the first embodiment shown in FIGS. 1 to 4 in that the by-pass conduit 15 is provided with a filter. The constituent elements same as those in the first embodiment are attached with the same reference numerals and descriptions thereof will be omitted.

As shown in FIG. 8, a filter 19 is provided to at least a part of the by-pass conduit 15.

The filter 19 allows only passage of a gas and blocks passage of liquids and solid substances. Specifically, the filter 19 allows the passage of only the gas, that is, only air A, among the gas D including the components derived from the living tissue, and removes the components derived from the living tissue and the liquids such as mucus, the solid substances such as residue, etc., in the body cavity B.

Note that the filter 19 is made of a known porous filter having a pore size of about 100 μm, for example, which allows the passage of gas and steam and prohibits the passage of solid substances and liquids. Note that the filter 19 may be made of a membrane filter, a cotton plug filter, a filter paper, a fiber membrane, or the like.

That is, when the gas D is sucked through the by-pass conduit 15, the components derived from the living tissue in the gas D and the liquids and solid substances in the body cavity B are removed by the filter 19, which prevents the components derived from the living tissue, the solid substances, and liquids from entering the by-pass conduit 15.

Note that the reason why only the air A in the gas D is allowed to pass through by the filter 19 is that the by-pass conduit 15 is a conduit to be used only for sucking the gas D and the diameter of the by-pass conduit 15 is formed to be small, as described above, and it is difficult to insert a cleaning tool such as a cleaning brush into the by-pass conduit 15, which leads to a difficulty in cleaning processing of the by-pass conduit 15. That is, the filter is provided for preventing the components derived from the living tissue in the gas D and the solid substances and liquids in the body cavity B from entering the by-pass conduit 15.

In view of such circumstances, it is preferable that the filter 19 is provided at a position as close as possible to the distal end side of the by-pass conduit 15.

In addition, a plurality of filters 19 may be provided to the by-pass conduit 15. For example, a plurality of filters 19 may be disposed at the by-pass conduit 15 and the pore sizes of the plurality of filters 19 may be gradually decreased in the order from the filter located on the distal-most side, to prevent the filter 19 disposed in the vicinity of the branched part of the by-pass conduit 15 from being clogged easily with the components derived from the living tissue and the like when a large amount of the gas D flows into the by-pass conduit 15.

Note that other configurations of the endoscope apparatus 1 are the same as those in the first embodiment. In addition, also in the present embodiment, a part of the by-pass conduit 15 may be exposed to the outside of the operation portion 3 similarly in the configuration shown in FIG. 5.

Thus, in the present embodiment, the by-pass conduit 15 is provided with the filter 19 that allows only the gas to pass through.

With such a configuration, the components derived from the living tissue and the liquids and solid substances in the body cavity B are removed by the filter 19, when the mist gas D including the components derived from the living tissue passes through the by-pass conduit 15, which prevents the components derived from the living tissue and the liquids and solid substances in the body cavity B from entering the by-pass conduit 15.

Such a configuration eliminates the need for performing cleaning processing with a cleaning brush and the like on the by-pass conduit 15 whose diameter is formed to be small, which leads to an improved cleaning performance of the by-pass conduit 15. Note that other effects are the same as those in the first embodiment described above.

In addition, the above-described first and second embodiments show a case where the mist gas D including the components derived from the living tissue, which is generated and filled in the body cavity B when the periphery of the lesional mucosa part S is resected by using the high-frequency knife 113 in the ESD procedure, is sucked through the by-pass conduit 15 as well as through the parts 10x, 10z of the suction conduit 10, as an example.

The first and second embodiments are not limited to the example, and it is needless to say that the configurations in the first and second embodiments are applicable to all the procedures for sucking the mist gas D including the components derived from the living tissue, which is filled in the body cavity B, through the by-pass conduit 15 as well as the parts 10x, 10z of the suction conduit 10, when cauterizing processing is performed by applying energy to the living tissue by the cauterizing device protruded in the body cavity B.

What is claimed is:

1. An endoscope apparatus comprising:
  an endoscope comprising:
    an insertion portion having a distal end and a proximal end, and inserted into a body from a distal end side;
    a first conduit for allowing fluids in the body to flow to outside the body through a suction port provided at the distal end side of the insertion portion;
    a second conduit through which, among the fluids in the body, a fluid generated in the body and including a solid particulate component passes, the second conduit being provided so as to be branched off from a first position on the first conduit and joined again with the first conduit;
    a first valve that opens and closes a flow passage of the first conduit, the first valve being provided to the first conduit at a location between a position where the second conduit is branched off and a position where the second conduit is joined; and
    a second valve that opens and closes a flow passage of the second conduit, the second valve being provided to the second conduit;

a cauterizing device that applies energy to a living tissue in the body to cauterize the living tissue; and a processor configured to cause the second valve to open and close based on an operation of the cauterizing device.

2. The endoscope apparatus according to claim 1, wherein the processor performs operation for opening the second valve in conjunction with a timing at which the cauterizing device applies the energy to the living tissue.

3. The endoscope apparatus according to claim 1, wherein the second conduit is branched off from the first position on the first conduit on a distal end side with respect to the first valve and joined again with a second position on the first conduit on a proximal end side with respect to the first valve.

4. The endoscope apparatus according to claim 1, wherein
the first conduit is connected with a suction device that sucks the fluids through the first conduit, and
when the processor opens the second valve, the fluids in the body passes through the second conduit by driving of the suction device.

5. The endoscope apparatus according to claim 1, wherein the second conduit is provided with a filter that allows passage of a gas and blocks passage of a liquid and a solid substance.

6. The endoscope apparatus according to claim 5, wherein the second conduit has a diameter smaller than a diameter of the first conduit.

7. The endoscope apparatus according to claim 1, wherein
the endoscope is provided with an operation portion provided continuously with the insertion portion, and
a part of the second conduit is exposed to an outside of the operation portion, and the second valve is provided at the part of the second conduit exposed to the outside of the operation portion.

8. The endoscope apparatus according to claim 1, wherein the first conduit also serves as a treatment instrument insertion channel that allows at least the cauterizing device to pass through into the body.

9. The endoscope apparatus according to claim 1, wherein the first valve is a valve that causes the flow passage of the first conduit to open and close actively by an operator.

10. The endoscope apparatus according to claim 1, wherein the processor is configured to:
perform image processing on an endoscope image acquired by the endoscope, and
when the processor determines that a concentration of mist in the endoscopic image exceeds a certain value based on a proportion of a white part in the endoscopic image, open the second valve.

11. The endoscope apparatus according to claim 1, wherein the processor performs operation for opening the second valve when humidity in the body, which is obtained from a humidity detection device provided at a distal end of the insertion portion of the endoscope, exceeds a certain value.

12. An endoscope comprising:
an insertion portion having a distal end and a proximal end, and inserted into a body from a distal end side;
a first conduit for allowing fluids in the body to flow to outside the body through a suction port provided at the distal end side of the insertion portion;
a second conduit through which, among the fluids in the body, a fluid generated in the body and including a solid particulate component passes, the second conduit being provided so as to be branched off from a first position on the first conduit and joined again with the first conduit;
a first valve that opens and closes a flow passage of the first conduit, the first valve being provided to the first conduit at a location between a position where the second conduit is branched off and a position where the second conduit is joined; and
a second valve that opens and closes a flow passage of the second conduit, the second valve being provided to the second conduit;
wherein the second valve is opened and closed based on an operation of a cauterizing device that cauterizes a living tissue in the body by applying energy to the living tissue.

* * * * *